United States Patent [19]

Smith et al.

[11] Patent Number: 4,777,166

[45] Date of Patent: * Oct. 11, 1988

[54] 2-ACETYLPYRIDINE THIOSEMICARBAZONE COMPOSITIONS AS ANITVIRAL AGENTS

[75] Inventors: Sandra H. Smith; John C. Drach; Gordon L. Flynn, all of Ann Arbor, Mich.

[73] Assignees: The United States of America as represented by the Secretary of the Army, Washington, D.C.; The Regents of The University of Michigan, Ann Arbor, Mich.

[ * ] Notice: The portion of the term of this patent subsequent to Jun. 22, 2003 has been disclaimed.

[21] Appl. No.: 846,174

[22] Filed: Mar. 31, 1986

Related U.S. Application Data

[63] Continuation-in-part of Ser. No. 363,723, Mar. 30, 1982, Pat. No. 4,596,798.

[51] Int. Cl.$^4$ .................... A61K 31/33; A61K 31/395
[52] U.S. Cl. .................... 514/183; 514/210; 514/218; 514/247; 514/250; 514/315; 514/344; 514/404; 514/512; 514/717; 514/731; 514/732; 514/737; 514/937; 514/237.2
[58] Field of Search ............... 514/183, 210, 218, 227, 514/247, 250, 315, 344, 408, 512, 717, 731, 732, 737, 937

[56] References Cited

U.S. PATENT DOCUMENTS 4,317,776 3/1982 Klayman et al. .................... 540/481
4,596,798 6/1986 Shipman et al. .................... 514/183

*Primary Examiner*—John Rollins
*Attorney, Agent, or Firm*—Francis A. Cooch; James H. Dautremont; Werten F. W. Bellamy

[57] ABSTRACT

This invention relates to various compositions, comprising a 2-acetylpridine thiosemicarbazone and a diol, which are useful in the treatment of viral infections.

68 Claims, 5 Drawing Sheets

2-ACETYLPYRIDINE THIOSEMICARBAZONE COMPOSITIONS AS ANTIVIRAL AGENTS

CROSS REFERENCE

This application is a continuation-in-part of U.S. patent application Ser. No. 363,723, filed Mar. 30, 1982, and now U.S. Pat. No. 4,596,798.

BACKGROUND OF THE INVENTION

The antiviral activity of thiosemicarbazones was first reported in 1950 by Hamre, et al., in *Proc. Soc. Exp. Biol. Med.*, Vol. 73, pp. 275–278. They found that derivatives of benzaldehyde thiosemicarbazone were active against neurovaccinial infection in mice when given orally. This prompted further investigation of other thiosemicarbazones. The thiosemicarbazone of isatin was found by Bauer in 1955 to be one of the most active as reported in *British J. Exp. Pathology*, Vol. 36, pp. 105–114, and a clinical trial of the N-methyl derivative of isatin-beta-thiosemicarbazone (methisazone) was carried out by Bauer and Associates in India. The studies indicated that the drug was effective in the prevention of smallpox in persons exposed to the disease. Although these studies have been widely accepted as evidence of the effective antiviral activity of methisazone in humans, a more recent field trial study reported on the 1971 by Heiner, et al., *Am. J. Epidemiology*, Vol. 94, pp. 435–449, demonstrated little efficacy in humans. The drug also has been used to treat patients with genital lesions caused by herpes simplex virus (HSV), but it had little effect on the severity or duration of the lesions as reported in 1964 by Hutfield, et al. in *Lancet*, Vol. 1, pp. 329–320.

In 1969, Sidwell and co-workers evaluated a series of purine analogs as antiviral agents and reported in *Proc. Soc. Exp. Biol. Med.*, Vol. 131, pp. 1223–1230 that purine-6-carboxaldehyde thiosemicarbazone was effective in suppressing both the cytopathic effect and the titers of human cytomegalovirus. This was the first report of a substituted thiosemicarbazone being active against a herpesvirus. In 1970, the effect of heterocyclic thiosemicarbazones was examined by Brockman, et al. and reported in *Proc. Soc. Exp. Biol. Med.*, Vol. 133, pp. 609–614. They tested the effect of several pyridine, isoquinoline, purine, and isatin derivatives on HSV and found that only those compounds in which the thiosemicarbazide moiety was affixed to the heterocyclic ring in the alpha position to the ring nitrogen were active. For example, beta-isatin, 3-formylpyridine, and 4-formylpyridine derivatives were inactive, whereas the 2-formylpyridine derivative was active.

According to the instant invention, applicants have demonstrated that selected 2-acetylpyridine thiosemicarbazones inhibit the replication of herpes simplex virus types 1 and 2 to a greater extent than cellular DNA (deoxyribonucleic acid) or protein synthesis. By using CsCl density gradient ultracentrifugation, we have been able to show that for the derivatives tested, viral DNA synthesis was inhibited to a greater extent that cellular DNA synthesis.

DETAILED DESCRIPTION OF THE INVENTION

Figure 1:
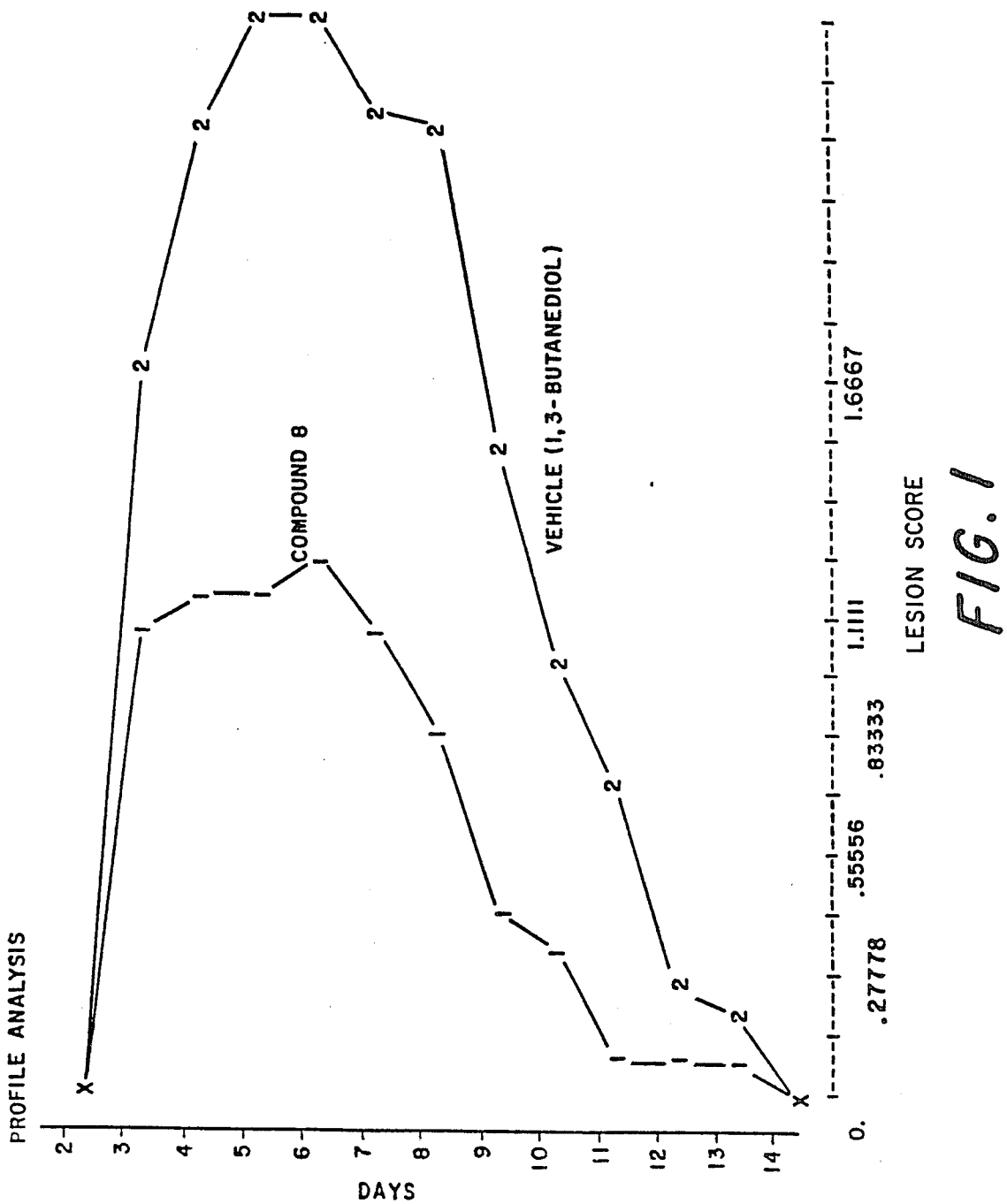

This invention relates to the use of composition of matter and their pharmaceutically-acceptable acid addition salts in the treatment of viral infections comprising a therapeutically-effective amount of:

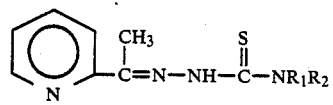

or a pharmaceutically-acceptable acid addition salt thereof wherein $R_1$ is hydrogen, alkyl, preferably having 1 to 12 carbon atoms or are, preferably 6 to 12 carbon atoms; cycloalkyl, preferably having 3 to 10 carbon atoms; substituted alkyl wherein the alkyl group preferably has 1 to 12 carbon atoms and the substituent group is amine, alkylamino (preferably 1 to 4 carbon atoms), dialkylamino (preferably 1 to 4 carbon atoms in each alkyl group), cycloalkyl (preferably 3 to 10 carbon atoms), hydroxy, C(O)Oalkyl (preferably 1 to 4 carbon atoms in the alkyl group), phenyl, or pyridyl; alkenyl, preferably having 2 to 6 carbon atoms; alkynyl, preferably having 3 to 6 carbon atoms; substituted benzyl wherein the substituent is methyl or phenyl on the alpha carbon atom, or the substituent is alkyl (preferably methyl), dialkyl (preferably dimethyl), halo, dihalo, or alkoxy (preferably ethoxy) on the phenyl ring; adamantyl; phenyl; naphthyl; substituted phenyl or substituted naphthyl wherein the ring is mono-, di-, or trisubstituted and the substituents are alkyl (preferably 1 to 4 carbon atoms), halo (preferably fluoro), alkoxy (preferably 1 to 4 carbon atoms), hydroxy, phenoxy, trifluoromethyl, dialkyl (preferably dimethyl) amino, dialkylaminoalkyl (preferably diethylaminomethyl), or C(O)Oalkyl (preferably 1 to 4 carbon atoms in the alkyl group); pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:

(1) alkylenimino;
(2) alkylenimino which may contain one double bond and/or is mono- or disubstituted with alkyl (preferably 1 to 4 carbon atoms), hydroxy, phenyl, or benzyl;
(3) alkylenimino which is either bridged by an alkylene group (preferably 2 carbon atoms) or is fused to a phenyl ring; or is attached by a spiro linkage to an ethylene ketal group;
(4) homopiperazinyl; homopiperazinyl substituted with alkyl (preferably 1 to 4 carbon atoms); piperazinyl; or piperazinyl substituted with alkyl (preferably 1 to 4 carbon atoms), dialkyl (preferably 1 to 4 carbon atoms in each alkyl group), phenyl, C(O)Oalkyl (preferably 1 to 4 carbon atoms in the alkyl group), trifluoromethylphenyl, halophenyl, benzyl, or pyridyl; and
(5) morpholino, dialkyl (preferably 1 to 4 carbon atoms in each alkyl group) morpholino.

When $R_1$ and $R_2$ are taken together with the nitrogen atom to which they are attached, the resulting heterocyclic ring is preferably one of the following: azetidino; pyrrolidino; 2,5-dimethylpyrrolidino; piperidino;

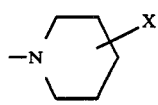

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethylpiperidino; 3,5-dimethyl piperidino; morpholino; 3,5-dimethylmorpholino;

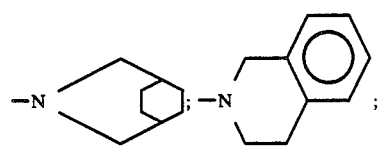

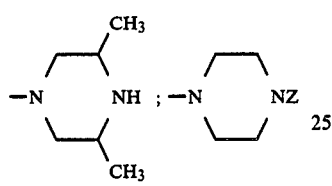

(wherein Z is methyl, phenyl, 3-trifluoromethylphenyl, benzyl, C(O))Et, 3-pyridyl, 2-pyridyl, or 4-fluorophenyl);

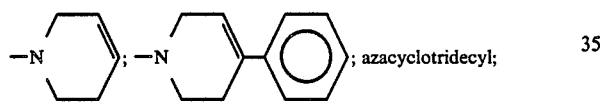

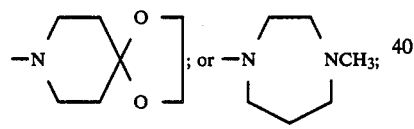

and a pharmaceutically-acceptable penetration-enhancing vehicle.

In this disclosure, it is understood that C(O)Oalkyl represents the alkyl carboxylic acid ester; for example, C(O)OEt represents the ethyl carboxylic acid ester.

A partial recitation of specific antiviral 2-acetylpyridine thiosemicarbazones contemplated within the scope of applicants' invention is depicted by the following formula:

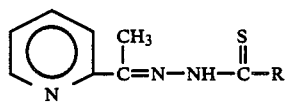

wherein R represents:

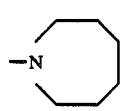    1.

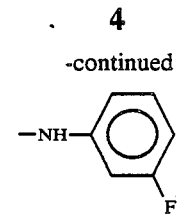    2.

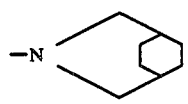    3.

—N—CH₂(CHOH)₄CH₂OH    4.
  |
  CH₃

—N(CH₃)₂    5.

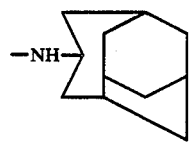    6.

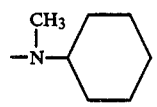    7.

—NHCH₃    8.

—NH₂    9.

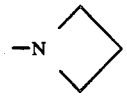    10.

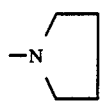    11.

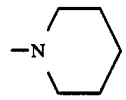    12.

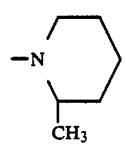    13.

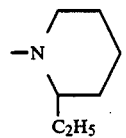    14.

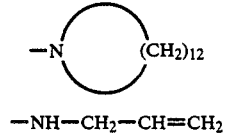    15.

—NH—CH₂—CH=CH₂    16.

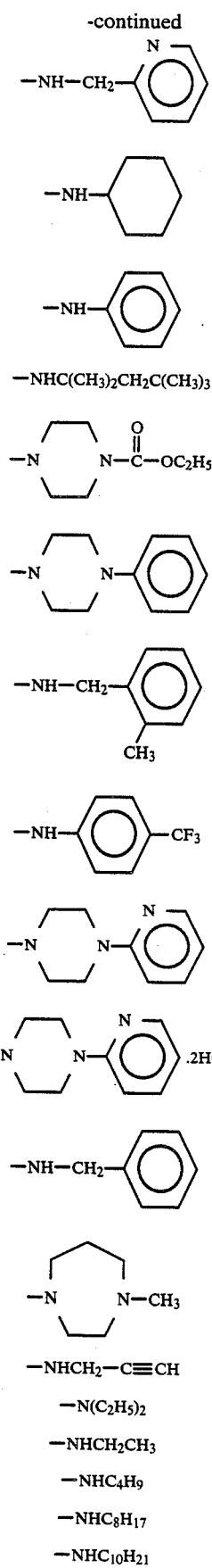
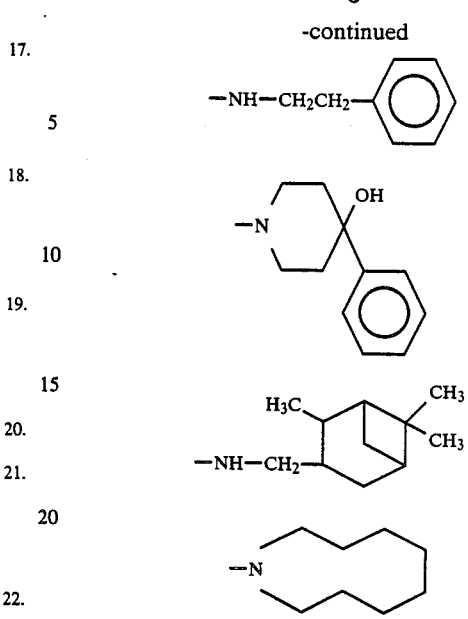

The chemical nomenclature for the antiviral 2-acetylpyridine thiosemicarbazones depicted in the preceding paragraph is as follows:

1. 1-Azacycloheptane-1-thiocarboxylic acid 2-1-(2-pyridyl)ethylidene hydrazide
2. 2-Acetylpyridine 4-(3-fluorophenyl)-3-thiosemicarbazone
3. 3-Azabicyclo[3.2.2]nonane-3-thiocarboxylic acid 2-1-(2-pyridyl)ethylidene hydrazide
4. 1-Methylamino-1-deoxy-D-glucitol-N-thiocarboxylic acid 2-1-(2-pyridyl)ethylidene hydrazide
5. 2-Acetylpyridine 4,4-dimethylthiosemicarbazone
6. 2-Acetylpyridine 4-(1-adamantyl)thiosemicarbazone
7. 2-Acetylpyridine 4-cyclohexyl-4-methylthiosemicarbazone
8. 2-Acetylpyridine 4-methylthiosemicarbazone
9. 2-Acetylpyridine thiosemicarbazone
10. Azetidine-1-thiocarboxylic acid 2-[1-(2-pyridyl)ethylidene]hydrazide
11. 1-Azacyclopentane-1-thiocarboxylic acid 2-[1-(2-pyridyl)ethylidene]hydrazide
12. Piperidine-1-thiocarboxylic acid 2-[1-(2-pyridyl)ethylidene]hydrazide
13. 2-Methylpiperidine-1-thiocarboxylic acid 2-[1-(2-pyridyl)ethylidene]hydrazide
14. 2-Ethylpiperidine-1-thiocarboxylic acid 2-[1-(2-pyridyl)ethylidene]hydrazide
15. 1-Azacyclotridecane-1-thiocarboxylic acid 2-[1-(2-pyridyl)ethylidene]hydrazide
16. 2-Acetylpyridine 4-allyl-3-thiosemicarbazone
17. 2-Acetylpyridine 4-(2-picolyl)-3-thiosemicarbazone
18. 2-Acetylpyridine 4-cyclohexyl-3-thiosemicarbazone
19. 2-Acetylpyridine 4-phenyl-3-thiosemicarbazone
20. 2-Acetylpyridine 4-(1,1,3,3-tetramethylbutyl)-3-thiosemicarbazone
21. 1,4-Diaza-4-carboethoxycyclohexane-1-thiocarboxylic acid 2-[1-(2-pyridyl)ethylidene]hydrazide
22. 1,4-Diaza-4-phenylcyclohexane-1-thiocarboxylic acid 2-[1-(2-pyridyl)ethylidene]hydrazide
23. 2-Acetylpyridine 4-(2-methylbenzyl)-3-thiosemicarbazone
24. 2-Acetylpyridine 4-(4-trifluoromethylphenyl)-3-thiosemicarbazone 25. 1,4-Diaza-4-(2-pyridyl)cyclohexane-1-thiocarboxylic acid 2-[1-(2-pyridyl)ethylidene]hydrazide
26. 1,4-Diaza-4-(2-pyridyl)cyclohexane-1-thiocarboxylic acid 2-[1-(2-pyridyl)ethylidene]hydrazide dihydrochloride
27. 2-Acetylpyridine 4-benzyl-3-thiosemicarbazone
28. 1,4-Diaza-4-methylcycloheptane-1-thiocarboxylic acid 2-[1-(2-pyridyl)ethylidene]hydrazide
29. 2-Acetylpyridine 4-(2-propynyl)-3-thiosemicarbazone
30. 2-Acetylpyridine 4,4-diethylthiosemicarbazone
31. 2-Acetylpyridine 4-ethylthiosemicarbazone
32. 2-Acetylpyridine 4-butylthiosemicarbazone
32. 2-Acetylpyridine 4-octylthiosemicarbazone
34. 2-Acetylpyridine 4-decylthiosemicarbazone
35. 2-Acetylpyridine 4-(2-phenethyl)thiosemicarbazone
36. (4-Hydroxy-4-phenylpiperidine)-1-thiocarboxylic acid 2-[1-(2-pyridyl)ethylidene]hydrazide
37. 2-Acetylpyridine 4-(3-pinylmethyl)thiosemicarbazone
38. 1-Azacyclononane-1-thiocarboxylic acid 2-[1-(2-pyridyl)ethylidene]hydrazide By "topical treatment", as used herein, is meant directly laying on or spreading on epidermal tissue, especially outer skin or membrane, including the skin or membrane of the vaginal or other body cavities.

By "therapeutically-effective amount", as used herein, is meant a sufficient amount of the composition to provide the desired immunosuppressive or anti-inflammatory effect and performance at a reasonable benefit/risk ratio attendant any medical treatment. Within the scope of sound medical judgment, the amount of pharmaceutically active composition used will vary with the particular condition being treated, the severity of the condition, the duration of the treatment, the specific compound employed, its concentration, the condition of the patients, concurrent therapies being administered, and like factors within the specific knowledge and expertise of the patient or the attending physician.

By "pharmaceutically-acceptble", as used herein, is meant the diol or acid addition salts of 2-acetylpyridine thiosemicarbazone compounds, as well as the other compatible drugs, medicaments or inert ingredients which the term describes that are suitable for use in contact with the tissues of humans and lower animals without undue toxicity, irritation, allergic response, and the like, commensurate with a reasonable benefit/risk ratio.

By the term "comprising", as used herein, is meant that various other compatible drugs and medicaments, as well as inert ingredients, occlusive agents, and cosmetic vehicles, can be conjointly employed in the compositions and processes of this invention, as long as the 2-acetylpyridine thiosemicarbazone and critical penetration enhancement vehicle is used. The term "comprising" thus encompasses and includes the more restrictive terms "consisting of" and "consisting essentially of" which characterize the use of the essential ingredients in the manner disclosed herein.

By "afflicted situs", as used herein, is meant a localized area of inflammation or lesion, and the immediately surrounding area.

By "application situs", as used herein, is meant a site suitable for application via a mechanical sustained release device or dressing.

By "penetration-enhancing", as used herein, is meant that the diol penetration enhancing vehicles of this composition provide marked transepidermal or percutaneous delivery of an incorporated 2-acetylpyridine thiosemicarbazone when compared to other vehicles of equal chemical potential.

The diol vehicles of the present invention significantly enhance the penetration of the 2-acetylpyridine compounds. Vehicles useful in the compositions and method of the instant invention include 1,2-propanediol; 1,3-propanediol; 1,2-butanediol; 1,3-butanediol; 1,4-butanediol, or mixtures of these diol compounds. Most preferably, 1,3-butanediol is used as the vehicle in the practice of this invention. It is understood that the use of other pharmaceutically-acceptable penetration-enhancing vehicles in combination with the diols are contemplated within the scope of the present invention.

An essential component of the compositions of the present invention is a therapeutically-effective amount of a 2-acetylpyridine thiosemicarbazone or a pharmaceutically-acceptable acid addition salt thereof. Based on the weight of the total composition (the 2-acetylpyridine thiosemicarbazone and penetration-enhancing vehicle), the vehicle is present in an amount from about 95 to about 99.9% by weight; more preferably about 97 to about 99.9% by weight; most preferably 99.3% by weight.

The compositions of the present invention may additionally contain other adjunct components conventionally found in pharmaceutical compositions, at their art-established usage levels. Thus, for example, the compositions may contain additional compatible pharmaceutically-active materials which enhance antiviral effectiveness or facilitate combination therapy (such as potentiating agents, antivirals, antimicrobials, antipruritics, astringents, local anesthetics or anti-inflammatory agents), or may contain materials useful in physically formulating various dosage forms of the composition of present invention, such as excipients, dyes, perfumes, fragrances, preservatives, antioxidants, opacifiers, thickening agents and stabilizers. These materials, when added, should not unduly interfere with the penetration enhancement of the compositions of this invention. Such formula modifications to improve cosmetic acceptability are well within the skill of workers in the cosmetic and dermatological arts and, by themselves, constitute no part of the present invention.

It can be seen from the foregoing that the compositions of the present invention admit to considerable variation, so long as the critical components, a 2-acetylpyridine thiosemicarbazone and diol compound, are present within the amounts indicated above and any undesirable affect on the therapeutic-effectiveness of the compositions of this invention are minimized.

The above-described 2-acetylpyridine thiosemicarbazone compounds of their pharmaceutically-acceptable acid addition salts are dissolved in a penetration-enhancing diol vehicle to form compositions which are useful in the topical treatment of viral infections caused by viruses. The viruses contemplated within the scope of this invention, susceptible to topical treatment with the above-described compositions, are quite extensive. For purposes of illustration, a partial listing of these viruses, with synonymous names in parentheses, include:

1. *Herpes simplex* virus type 1 (*Herpes labialis;* fever blisters; cold sores; *Herpesvirus hominis* type 1)
2. *Herpes simplex* virus type 2 (*Herpes genitalis; Herpesvirus hominis* type 2)

3. *Varicella-zoster* virus (varicella, zoster; chickenpox; shingles)

In addition to the viruses listed above, Epstein-Barr virus and Cytomegalovirus are known to afflict man. With the exception of the Epstein-Barr virus and Cytomegalovirus, herpesviruses have a tendency to infect derivatives of the ectoderm. Hence, these infections manifest skin, mucous membranes, eyes or nervous system involvement. Some of the herpesviruses possess oncogenic potential. Another characteristic of herpes viruses is that they may establish latent infections, which may become reactivated after variable periods of quiescence. Thus, the recurrence of herpes infections may be stimulated by fever, menstruation, exposure to sunlight (ultraviolet irradiation), emotional upsets, or intercurrent infections.

With respect to the pharmaceutically-acceptable acid addition salts of this invention, it will be apparent to those of ordinary skill in the art that such salts are contemplated only where the structural features of the compounds permit their preparation. As non-limiting examples of acids used to prepare such salts, hydrochloric and hydrobromic acids are representative.

Synthetic Procedures

Three synthetic procedures proved to be useful for preparing the thiosemicarbazones of this invention. In Scheme A, a primary amine was converted to the corresponding isothiocyanate (1), ordinarily by employing thiophosgene. Reaction of 1 with hydrazine afforded a thiosemicarbazide 2. Condensation of this intermediate with 2-acetylpyridine provided the 4-monosubstituted thiosemicarbazone 3. However, only thiosemicarbazones monosubstituted at position 4 can be prepared in this manner, Scheme A

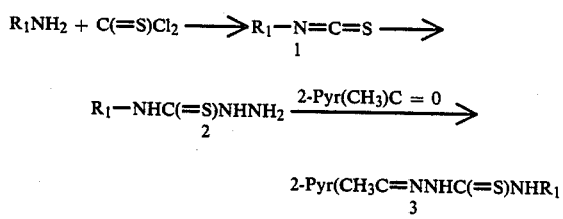

as 2-acetylpyridine proved to be usually resistant to condensation with 2,4-disubstituted thiosemicarbazides.

In Scheme B, reaction of hydrazine and carbon disulfide in the presence of sodium hydroxide yielded a carbodithioate. Alkylation of this carbodithioate with either iodomethane or dimethyl sulfate gave methyl hydrazinecarbodithioate (4). Condensation of 4 with 2-acetylpyridine gave the versatile intermediate, methyl 3-[1-(2-pyridyl)ethylidene]hydrazinecarbodithioate, 5. Reaction of 5 with primary amines gave 4-monosubstituted thiosemicarbazones such as 3 while secondary amines or cyclic amines produced 4,4-disubstituted thiosemicarbazones, 6. In addition, reaction of 5 was not limited to more active nucleophiles, as excellent yields could be obtained with many primary aromatic amines. However, 5 was resistant to reaction with some secondary aromatic amines, such as N-methylaniline.

Scheme B

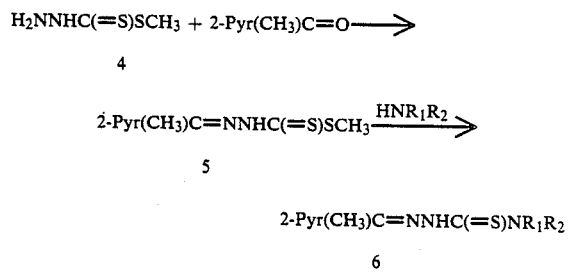

Scheme C involved the reaction of 2-acetylpyridine with hydrazine to yield the hydrazone 7. Reaction of this hydrazone with an isothiocyanate 1 produced a 4-monosubstituted thiosemicarbazone 3. This reaction was especially useful when the required isothiocyanate was commercially available.

Scheme C

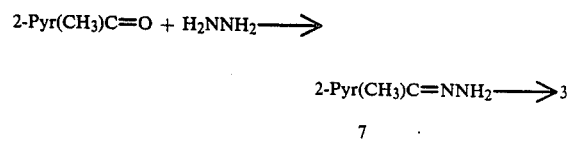

EXAMPLES

The working examples set forth below illustrate, without any implied limitation, the preparation of representative compounds and salts useful in the practice of this invention in the treatment of viral infections.

MATERIALS AND TEST METHODS

Laboratory Studies

The source of cells and HSV-1 (HF strain), the routine growth and passage of BHK-21/4 cells and KB cells, the propagation and titration of HSV, the techniques used for the enumeration of cells, and the detection of mycoplasma contamination were described in *Antimicrob. Agents Chemother*, Vol. 9, pp. 120–127 (1976).

The 2-acetylpyridine thiosemicarbazones were evaluated by means of a series of biochemical tests and virological assays. In brief, the testing procedure consisted of examining the effects of candidate substances on titers of HSV-1 and HSV-2 undergoing replication and on a battery of four biochemical tests to determine the effects of the candidate substances on cellular growth and metabolism as measures of cytotoxicity. The four biochemical tests were (i) [$^3$H]amino acid incorporation into acid-precipitable material, (ii) [$^3$H]thymidine incorporation into acid-precipitable material, (iii) DNA synthesis as measured by diphenylamine assays as described by Burton in *Methods Enzymol.*, Vol. 12, pp. 163–166 (1968), and (iv) protein synthesis as measured by Lowry assays using the procedure outlined in *J. Biol. Chem.*, Vol. 193, pp. 265–275 (1951).

The effect of drugs on HSV replication in KB cells was measured as previously described by Drach and Shipman in *Ann. N. Y. Acad. Sci.*, Vol. 284, pp. 396–406, by assaying in BHK-21/4 cells the number of plaque-forming units of newly synthesized virus.

For biochemical cytotoxicity measurements, KB cells were planted in glass scintillation vials employing the methods of Ball, et al. and Fujimoto, et al. as described in *Methods Cell Biol.*, Vol. 7, pp. 349–360 (1973) and *In Vitro*, Vol. 13, pp. 237–244 (1977), respectively. After a 4 to 5-hour incubation at 37° C. to allow attachment of the cells, some of the vials were rinsed with cold saline and stored at 4° C. to be used subsequently as initial samples in the determination of total protein and total DNA. The medium was removed from the remaining vials, and 2 ml of assay medium was added. Assay medium consisted of minimal essential medium with Earle salts containing 25 mM N-2-hydroxyethylpiperazine-N'-2-ethanesulfonic acid (HEPES), 0.127 g of L-arginine per liter, 10% calf serum, appropriate 0.5-log concentrations of drug or control medium, and 0.2 microcuries of either [$^3$H]thymidine or [$^3$H]amino acid mixture per ml. After an additional 18 to 22-hour incubation at 37° C., the liquid contents of the vials were aspirated, and the cell sheets were washed twice in ice-cold HEPES-buffered saline as described by Shipman in *Proc. Soc. Exp. Biol. Med.*, Vol. 130, pp. 305–310 (1969), three times with 1.5% perchloric acid, and once with 95% ethanol. After the addition of 10 ml of 2,5-diphenyloxazole (PPO)-toluene cocktail, the vials were counted in a Beckman LS8100-Texas Instruments 733ASR liquid spectrometer system as described by Shipman and Drach in *Science*, Vol. 200, pp. 1163–1165 (1978).

After counting, the cocktail was decanted, and the vials were washed three times with 95% ethanol and twice with glass-distilled water. One-half of the vials were used to determine the amount of total protein by the Lowry method reported in 1951 in *J. Biol. Chem.*, Vol. 193, pp. 265–275. The initial amount of protein present before the labeling period was begun was determined by using the initial sample vials which had been treated in a manner identical to that used for the incubated vials. This value was substracted from the values for the control and drug-containing vials.

The remaining vials were used in a determination of total DNA by the diphenylamine method described in 1968 by Burton and Shipman in *Methods Enzymol.*, Vol. 12, pp. 163–166. The initial amount of DNA present before the labeling period was determined from the vials stored at the start of the labeling period and was subtracted from the control and drug-containing samples.

Dose-response relationships were constructed by linearly regressing log drug concentrations against the percent inhibition values derived from viral replication, incorporation of [$^3$H]thymidine or [$^3$H]amino acids, total protein, or total DNA. The 50% inhibitory concentrations and corresponding 95% confidence intervals were calculated from the regression lines by using a method previously described in 1977 by Drach and Shipman, *Ann. N. Y. Acad. Sci.*, Vol. 284, pp. 396–406. Samples containing arabinosyladenine (vidarabine) at a concentration of 10 micrograms/ml were included in all assays as positive controls. Results from sets of assays were rejected whenever inhibition by arabinosyladenine deviated from its means response by more than 1.5 standard deviations.

Animal Studies

Adult female guinea pigs weighing 300–400 g were shaved, depilated chemicall, washed and dried under anesthesia (Innovar). The hairless area was divided into six squares with a marking pen. In the center of each area 25 microliters of a low passage clinical isolate of HSV at a titer of $3.2 \times 10^6$ PFU/ml was applied. The virus was inoculated under anesthesia with a spring-loaded vaccination instrument (Sterneedle Gun, Panray Division, Ormont Drug Co., Englewood, N. J.), which was released 12 times producing inoculation 0.75 mm deep on each skin area. The procedure is essentially according to Schafer, et al. in *Ann. N. Y. Acad. Sci.*, Vol. 284, pp. 624–631 (1977) and Alenius and Oberg in *Arch. Virol.*, Vol. 58, pp. 277–288 (1978).

Three to five areas on each animal were treated topically twice per day for five days beginning 24 hours after inoculation with varying concentrations of antiviral drugs as solutions or suspensions. 1,3-Butanediol was used as a vehicle. Two areas on each animal received solvent alone and served as the control sites. When different substituted thiosemicarbazones were compared, one area on each animal was used for each substance. Seven parallel areas (seven animals) were used in most experiments. Trisodium phosphonoformate, an antiviral drug known to be active in this system as reported in *Antimicrob. Agents and Chemother.*, Vol. 14, pp. 408–413 (1978) was included as a positive control. Any dermal toxicity due to the test compounds was noted.

To quantitate the effect of antiviral compounds, the scoring system of Alenius and Oberg as described in *Arch. Virol.*, Vol. 58, pp. 277–288 (1978) was used. After inoculation of the guinea pigs with HSV as described above, the inoculated areas were scored once daily for 14 days. The animals were depilated every three or four days to facilitate observation. All scoring was done blind. Time to healing was also noted for each drug. The statistical program employed to analyze the data used techniques of profile analysis, paired t-tests and analysis of variance.

Virus titers in infected skin were measured to confirm that the drugs inhibited viral replication and were not simply anti-inflammatory agents. Guinea pigs were sacrificed and the individual areas of inoculation sites were excised. Skin samples were frozen and thawed three time, minced with scissors, ground with sterile sand and HEPES-buffered saline (pH 7.4) containing 100 Units and 100 micrograms of penicillin and streptomycin, respectively, per ml. The suspensions were stored at $-76°$ C. for subsequent assay in BHK-21/4 cells according to the procedure of Shipman, et al. reported in *Antimicrob. Agents Chemother.*, Vol. 9, pp. 120–127 (1976).

Test Results

Several tests have been made to determine the activity of the compounds of this invention. In order to guide one of ordinary skill in the practice of the invention, these tests are described below, as well as results obtained in each test with a representative sampling of compounds. 2-Acetylpyridine thiosemicarbazones which appear in Table 1 are as follows:

COMPOUNDS

Number 1

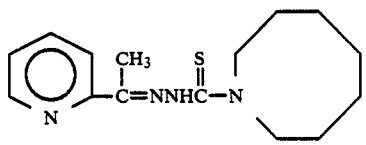

1H-Hexahydroazepin-1-thiocarboxylic acid
2-[1-(2-pyridyl)ethylidene]hydrazide

Number 2

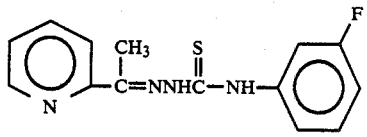

2-Acetylpyridine 4-(3-fluorophenyl)thiosemicarbazone

Number 3

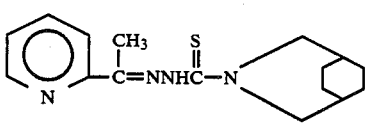

3-Azabicyclo[3.2.2]nonane-3-thiocarboxylic acid
2-[1-(2-pyridyl)ethylidene]hydrazide Number 4

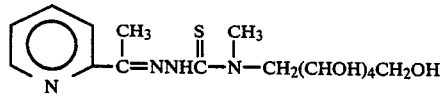

1-Methylamino-1-deoxy-D-glucitol-N-thiocarboxylic
acid 2-[1-(2-pyridyl)ethylidene]hydrazide Number 5

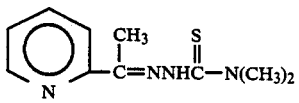

2-Acetylpyridine 4,4-dimethylthiosemicarbazone

Number 6

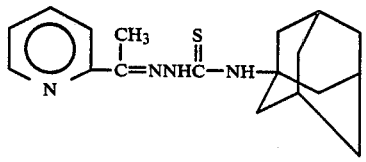

2-Acetylpyridine 4-(1-adamantyl)thiosemicarbazone

Number 7

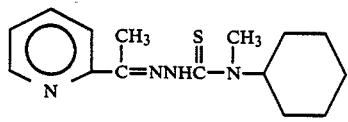

2-Acetylpyridine
4-cyclohexyl-4-methylthiosemicarbazone

Number 8

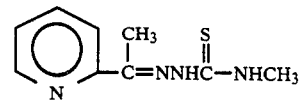

2-Acetylpyridine 4-methylthiosemicarbazone

Number 9

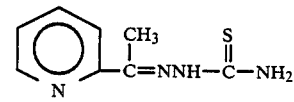

2-Acetylpyridine thiosemicarbazone

Animal Studies

In FIG. 1, the effect of topical treatment with 2-acetylpyridine 4-methylthiosemicarbazone (Compound Number 8) on cutaneous herpes simplex virus infection on guinea pigs is illustrated. Infected skin areas (HSV-1, Schering strain), seven areas for each type of treatment, were scored daily and the arithmetic mean for each day after inoculation is given. Treatment was started four hours post inoculation and consisted of four daily applications of 50 microliters of 0.7% 2-acetylpyridine 4-methylthiosemicarbazone or vehicle alone for five days.

Figure 2:
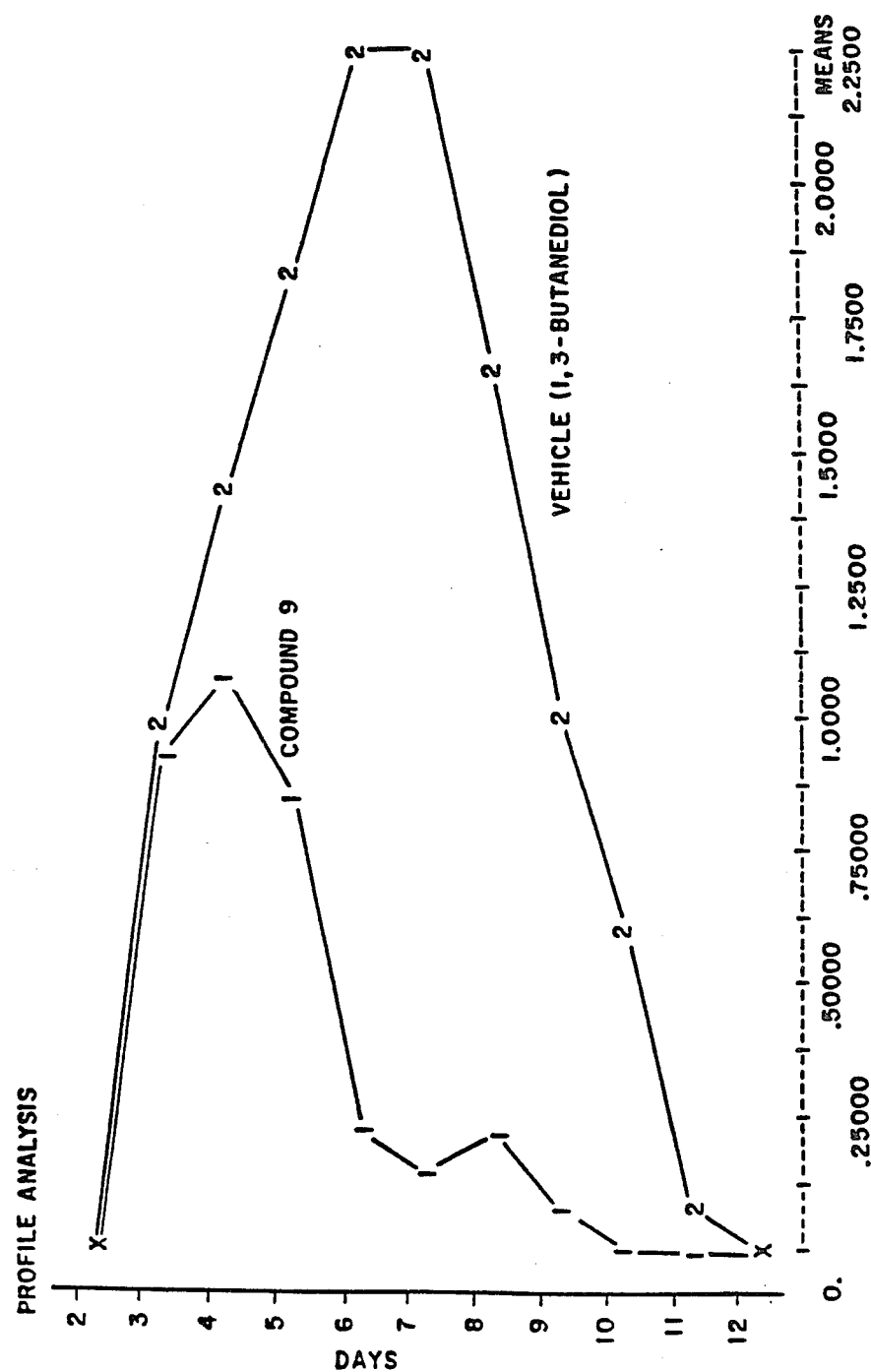

FIG. 2 illustrates the effect of topical treatment with 2-acetylpyridine thiosemicarbazone (Compound Number 9) on cutaneous herpes simplex virus infection on guinea pigs. Infected skin areas (HSV-1, Schering strain), seven areas for each type of treatment, were scored daily and the arithmetic mean for each day after inoculation is given. Treatment was started 24 hours post inoculation and consisted of two daily applications of 50 microliters of 0.7% the compound or vehicle alone for five days.

Figure 3:
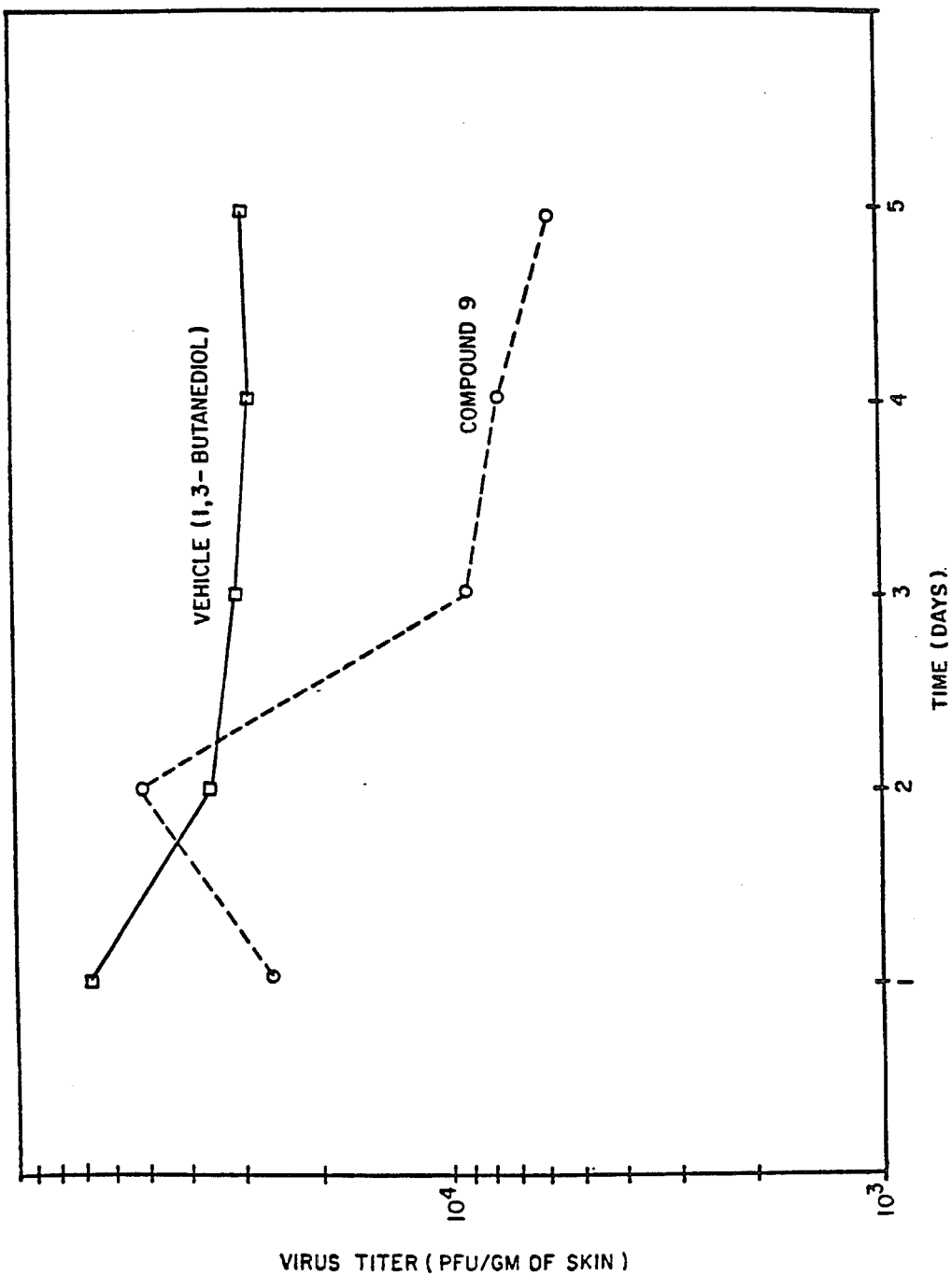

FIG. 3 illustrates the effect of topical treatment with 2-acetylpyridine thiosemicarbazone (Compound Number 9) on virus titer in the skin of herpes simplex virus-infected guinea pigs. the guinea pigs were inoculated with 25 microliters of a $1 \times 10^7$ PFU/ml suspension of HSV-1 (Schering strain). Treatment was started four hours post inoculation and consisted of four daily applications of 50 microliters of 0.7% of 2-acetylpyridine thiosemicarbazone (Compound Number 9) or vehicle alone.

Figure 4:
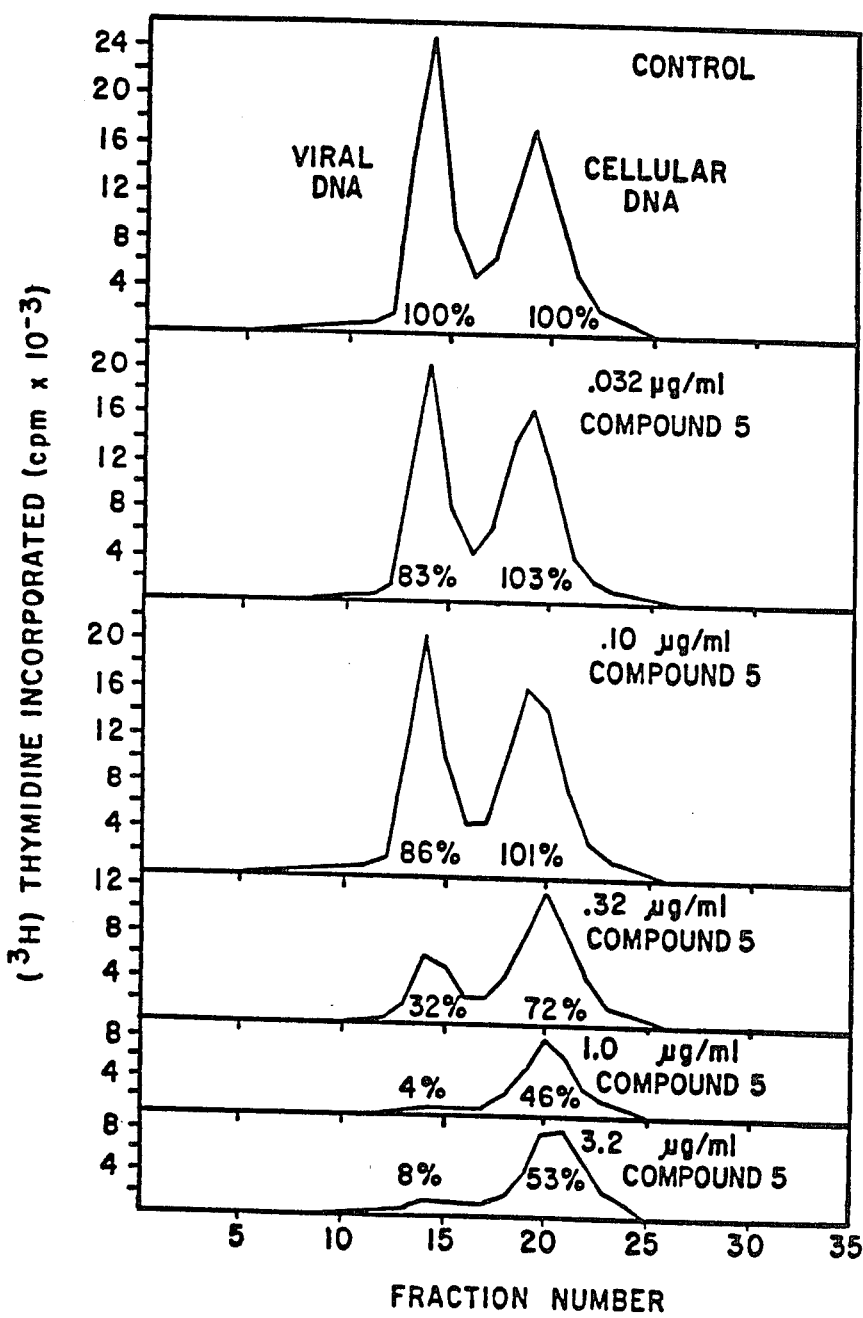

FIG. 4 illustrates the separation of viral and cellular deoxyribonucleic acid (DNA) from cells infected with herpes simplex virus-1 by isopycnic centrifugation in CsCl gradients. The presence of selected concentrations of 2-Acetylpyridine 4,4-dimethylthiosemicarbazone (Compound Number 5) is expressed as a percentage of the amount incorporated into the respective DNA species in cell cultures without drug (top control panel).

Figure 5:
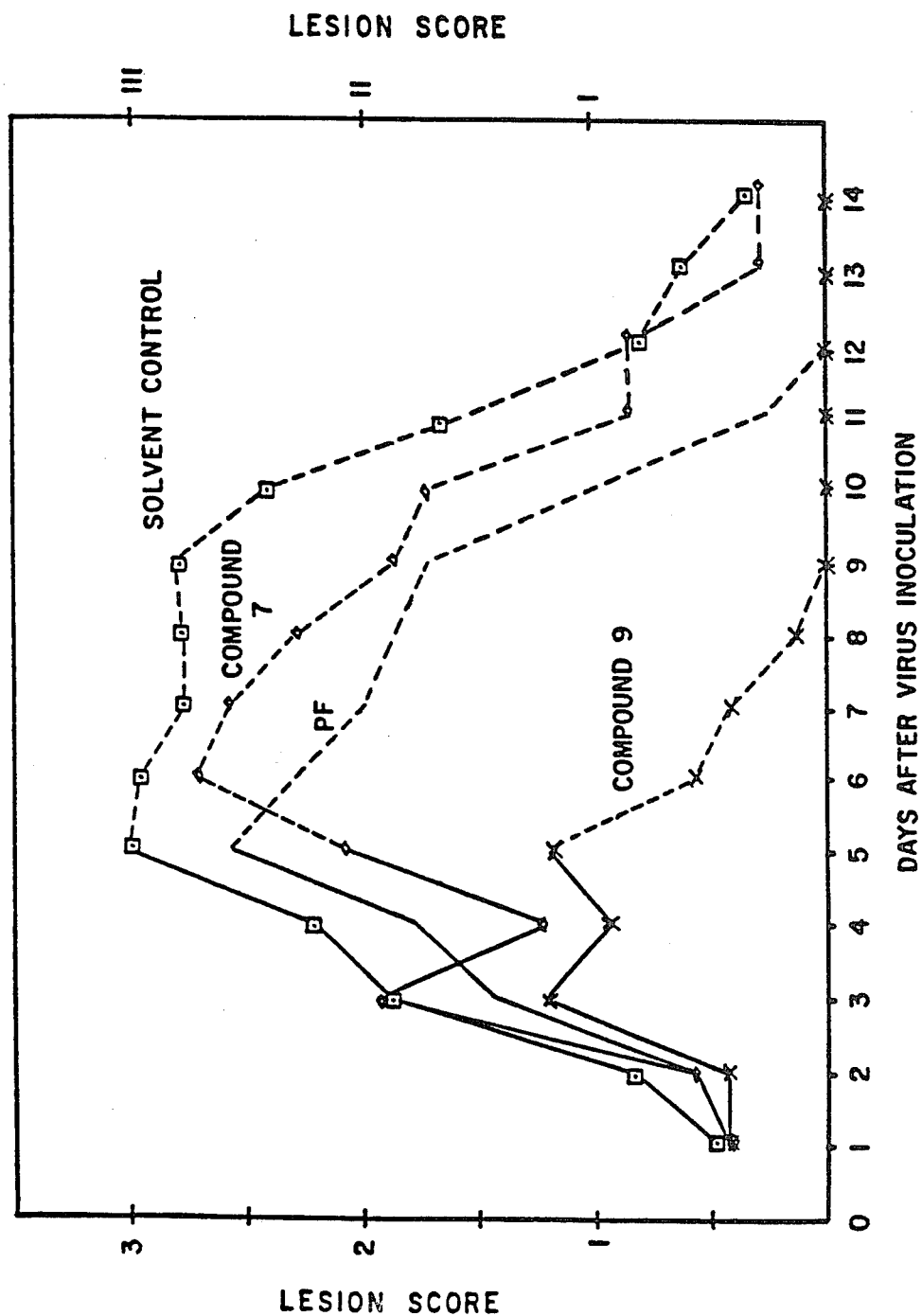

FIG. 5 illustrates the relative therapeutic effect of 2-acetylpyridine thiosemicarbazone (Compound Number 9), 2-acetylpyridine 4-cyclohexyl-4-methylthiosemicarbazone (Compound Number 7), and phosphonoformate. Infected skin areas (seven areas for each type of treatment), were scored daily and the arithmetic mean for each day after inoculation is given. Treatment was started 24 hours following inoculation and consisted of two daily applications of 50 microliters for five days, resulting in a total of 10 applications.

Laboratory Studies

Among the 2-acetylpyridine thiosemicarbazones tested, 2-acetylpyridine 4-methylthiosemicarbazone was tested against HSV-1 in the 15-day guinea pig model. Using 0.7% of this compound resulted in a significant reduction in lesion score as indicated in FIG. 1.

The derivatives listed in Table 1 were subjected to a biochemical battery of tests and the resultant 50% inhibitory concentrations were compared with concentrations required to inhibit viral replication by 50%. In terms of apparent therapeutic indices, a range of 1 to 114 was seen for HSV-1 while a range of 3.7 to 160 was calculated for HSV-2 based on the derivatives tested.

Surprisingly, 2-acetylpyridine 4-methylthiosemicarbazone produced significant cures in HSV-1 infected guinea pigs without undesirable side effects and had the highest apparent therapeutic index. This compound did not produce erythema or induration when applied topically. Moreover, other derivatives such as 2-acetylpyridine thiosemicarbazone, produced only a slight dermal toxicity when tested against HSV-1 in the 15-day guinea pig model. The use of 0.7% of the compound resulted in a dramatic reduction in lesion score as illustrated in FIG. 2. This compound demonstrated antiviral efficacy in the skin of HSV-1 infected guinea pigs. More precisely, at days 3, 4, and 5 a significant reduction in virus titer was noted in animals treated topically with 2-acetylpyridine thiosemicarbazone as indicated in FIG. 3.

Example 1

2-Acetylpyridine 4-allyl-3-thiosemicarbazone (Procedure C)

A solution of 2.7 g (0.02 mol) of 2-acetylpyridine hydrazone in 5 ml of MeOH was treated with 3.1 g (0.03 mol) of allyl isothiocyanate and the solution was heated at reflux for 3 hours. The solution was cooled and the product which formed was collected. The crude material was recrystallized 3 times from MeOH, affording 2.5 g (49%) of white needles of 2-acetylpyridine 4-allyl-3-thiosemicarbazone, mp 107° C.

Analysis Calcd. for $C_{11}H_{14}N_4S$: C, 56.38; H, 6.02; N, 23.91; S, 13.68. Found: C, 56.09; H, 6.11; N, 24.36; S, 13.89.

Example 2

2-Acetylpyridine 4-cyclohexyl-3-thiosemicarbazone (Procedure C)

A solution of 6.76 g (0.05 mol) of 2-acetylpyridine hydrazone in 10 ml of MeOH was treated with 7.2 g (0.05 mol) of cyclohexyl isothiocyanate and the solution was heated at reflux for 3 hours. The solution was chilled, and the crystals which formed were collected. Recrystallization of the product from 150 ml of MeOH afforded 6.40 g (46%) of white needles of 2-acetylpyridine 4-cyclohexyl-3-thiosemicarbazone, mp 155° C.

Analysis Calcd. for $C_{14}H_{20}N_4S$: C, 60.84; H, 7.29; N, 20.27; S, 11.60. Found: C, 60.76; H, 7.19; N, 20.16; S, 11.73.

Example 3

2-Acetylpyridine 4-(2-diethylaminoethyl)-3-thiosemicarbazone dihydrobromide (Procedure A)

By the application of the procedure of R. S. McElhinney J. Chem. Soc. (c), 950 (1966), 2-diethylaminoethyl isothiocyanate, (bp 54°–55° C./1.5 mm Hg), was prepared in 20% yield.

Analysis Calcd. for $C_7H_{14}N_2S$: C, 53.12; H, 8.92; N, 17.70; S, 20.26. Found: C, 52.97; H, 8.76; N, 18.01; S, 20.47.

A solution of 1 g (0.063 mol) of 2-diethylaminoethyl isothiocyanate in 5 ml of MeCN was treated with 0.3 g (0.063 mol) of 85% hydrazine hydrate. The solution was heated at reflux for 10 minutes and the solvent was removed under reduced pressure. The residue was then recrystallized from $C_6H_6$ affording 750 mg (63%) of white needles of 4-(2-diethylaminoethyl)-3-thiosemicarbazide, mp 83°–83.5° C.

Analysis Calcd. for $C_7H_{18}N_4S$: C, 44.18; H, 9.53; N, 29.44 S, 16.85. Found: C, 44.19; H, 9.46; N, 29.56; S, 16.60.

A solution of 605 mg (5 mmol) of 2-acetylpyridine in 10 ml of MeCN was treated with 950 mg (5 mmol) of 4-(2-diethylaminoethyl)-3-thiosemicarbazide and the solution was heated at reflux for 10 hours. The pH of the solution was adjusted to 6 with concentrated HBr and diluted with 15 ml of $Et_2O$. An oil which separated from solution soon solidified. Crystallization of this product from MeOH-MeCN afforded 1.42 g (64%) of yellow crystals of 2-acetylpyridine 4-(2-diethylaminoethyl)-3-thiosemicarbazone dihydrobromide, mp 231° C.

Analysis Calcd. for $C_{14}H_{23}N_5S$ 2HBr: C, 36.93; H, 5.54; N, 15.38; S, 7.04. Found: C, 36.99; H, 5.52; n, 15.30; S, 7.07.

Example 4

2-Acetylpyridine 4-(3-fluorophenyl)-3-thiosemicarbazone (Procedure A)

2-Acetylpyridine (2.0 g, 0.0165 mol) in 70 ml of EtOH and 2.78 g (0.015 mol) 4-(3-fluorophenyl)-3-thiosemicarbazide (mp 152°–155° C.) were heated at reflux temperature for 4 hours. The solution was refrigerated overnight and the product was collected. Recrystallization from MeCN afforded 1.1 g (25%) of 2-acetylpyridine 4-(3-fluorophenyl)-3-thiosemicarbazone, mp 159°–160° C.

Analysis Calcd. for $C_{14}H_{13}FN_4S$: C, 58.32; H, 4.54; N, 19.43; S, 11.12. Found: C, 57.87; H, 470; N, 19.41; S, 11.08.

Example 5

2-Acetylpyridine 4,4-diisobutyl-3-thiosemicarbazone (Procedure B)

A solution of 10 g (0.044 mol) of methyl 3-[1-(2-pyridyl)ethylidene]hydrazinecarbodithioate in 25 ml of MeOH was treated with 7.5 g (0.058 mol) of diisobutylamine and heated at reflux for 6 hours. The solution was chilled and the crystals which formed were collected. Recrystallization from 130 ml of heptane afforded 8.6 g (64%) of yellow needles of 2-acetylpyridine 4,4-diisobutyl-3-thiosemicarbazone, mp 96° C.

Analysis Calcd. for $C_{16}H_{26}N_4S$: C, 62.71; H, 8.55; N, 18.28; S, 10.46. Found: C, 63.27; H, 8.50; N, 18.14; S, 10.21.

Example 6

Azacycloheptane-1-thiocarboxylic acid 2-[1-(2-pyridyl)ethylidene]hydrazide (Procedure B)

A solution of 5.0 g (0.022 mol) of methyl 3-[1-(2-pyridyl)ethylidene]hydrazinecarbodithioate in 15 ml of MeOH was treated with 2.2 g (0.022 mol) of hexamethylenimine and heated at reflux for 5 hours. The solution was chilled, scratched and the product which separated was collected. Recrystallization from 150 ml of MeOH afforded 3.4 g (56%) of yellow needles of azacycloheptane-1-thiocarboxylic acid 2-[1-(2-pyridyl)ethylidene]hydrazide, mp 165° C.

Analysis Calcd. for $C_{14}H_{20}N_4S$: C, 60.84; H, 7.29; N, 20.27 S, 11.60. Found: C, 60.91; H, 7.20; N, 20.30; S, 11.89.

Example 7

3-Azabicyclo 3.2.2 heptane-3-thiocarboxylic acid 2-[1-(2-pyridyl)ethylidene]hydrazide (Procedure B)

A solution of 3.8 g (0.018 mol) of methyl 3-[1-(2-pyridyl)ethylidene]hydrazinecarbodithioate and 2.1 g (0.017 mol) of 3-azabicyclo[3.2.2]nonane was heated at reflux for 5 hours. The solution was cooled, and the product which crystallized was collected. Recrystallization from 160 ml of MeOH afforded 3.34 g (65%) of yellow needles of 3-azabicyclo[3.2.2]nonane-3-thiocarboxylic acid 2-[1-(2-pyridyl)ethylidene]hydrazide, mp 156° C.

Analysis Calcd. for $C_{16}H_{22}N_4S$: C, 63.54; H, 7.33; N, 18.53; S, 10.60. Found: C, 63.51; H, 7.25; N, 18.55; S, 10.67.

Example 8

2-Acetylpyridine 4-cyclohexyl-4-methyl-3-thiosemicarbazone (Procedure B)

A solution of 10 g (0.44 mol) of methyl 3-[1-(2-pyridyl)ethylidene]hydrazinecarbodithioate in 25 ml of MeOH was treated with 7.5 g (0.066 mol) of N-methylcyclohexylamine and the solution heated at reflux for 8 hours. The solution was cooled overnight and the product which crystallized was collected. Recrystallization from cyclohexane afforded 9.3 g (72%) of 2-acetylpyridine 4-cyclohexyl-4-methyl-3-thiosemicarbazone, mp 96° C.

Analysis Calcd. for $C_{15}N_{22}N_4S$: C, 62.03; H, 7.64; N, 19.29; S, 11.04. Found: C, 62.07, H, 7.74; N, 19.23; S, 11.14.

Example 9

2-Acetylpyridine 4-(2-methylbenzyl)-3-thiosemicarbazone (Procedure B)

Methyl 3-[1-(2-pyridyl)ethylidene]hydrazinecarbodithioate (4.51 g, 0.02 mol) and 3.64 g (0.03 mol) 2-methylbenzylamine in 25 ml of methanol were heated under reflux for 36 hours followed by overnight regrigeration. The solid material which separated from solution was collected by filtration and recrystallized 3 times from ethanol to afford 3.85 g (48% of white crystalline 2-acetylpyridine 4-(2-Methylbenzyl)-3-thiosemicarbazone having a melting point of 152°-154° C.

Analysis Calcd. for $C_{16}H_{18}N_4S$: C, 64.40; H, 6.08; N, 18.78; S, 10.74. Found: C, 64.17; H, 6.23; N, 19.14; S, 10.64.

Example 10

4-(2-Pyridyl)-1-piperazinethiocarboxylic acid 2-[1-(2-pyridyl)ethylidene]hydrazide (Procedure B)

Methyl 3-[1-(2-pyridyl)ethylidene]hydrazinecarbodithioate (3.60 g, 0.016 mol) in 40 ml of EtOH was combined with 3.60 g (0.02 mol) of 1-(2-pyridyl)piperazine. The solution was heated at reflux for 18 hours, cooled and the yellow product which separated was collected. Recrystallization from MeCN afforded 3.45 g (60%) of 4-(2-pyridyl)-1-piperazinethiocarboxylic acid 2-[1-(2-pyridyl)ethylidene]hydrazide, mp 187°-188° C.

Analysis Calcd. for $C_{17}H_{20}N_6S$: C, 59.98; H, 5.92; N, 24.69; S, 9.42. Found: C, 60.65; H, 5.90; N, 24.61; S, 9.41.

Example 11

2-Acetylpyridine 4-(2-pyridyl)-3-thiosemicarbazone (Procedure A)

4-(2-Pyridyl)-3-thiosemicarbazide (1.68 g, 0.01 mol) in 125 ml of EtOH and 7.5 ml of glacial acetic acid was treated with 1.21 g (0.01 mol) of 2-acetylpyridine. The solution was heated at reflux for 3 hours, cooled and the product collected. Recrystallization from MeOH afforded 1.8 g (66%) of 2-acetylpyridine 4-(2-pyridyl)-3-thiosemicarbazone, mp 185°-187° C.

Analysis Calcd. for $C_{13}H_{13}N_5S$: C, 57.54; H, 4.83; N, 25.81; S, 11.82. Found: C, 57.03; H, 5.08; N, 25.96; S, 12.17.

Example 12

2-Acetylpyridine 4-(1-adamantyl)-3-thiosemicarbazone (Procedure A)

A solution of 1.5 g (0.03 mol) of hydrazine hydrate in 50 ml of EtOH was treated with 3.86 g (0.02 mol) of 1-adamantyl isothiocyanate, and stirred for one hour at room temperature. The product was collected and washed two times with EtOH, affording 4.33 g (96%) of 4-(1-adamantyl)-3-thiosemicarbazide, mp 206°-207° C. This thiosemicarbazide is disclosed in *Chemical Abstracts*, 70:11223 (1969); and in the U.S. Pat. No. 3,406,180.

2-Acetylpyridine (2.65 g, 0.022 mol) in 50 ml of EtOH and 2 ml of glacial acetic acid was combined with 4.33 g (0.0195 mol) of 4-(1-adamantyl)-3-thiosemicarbazide, and the solution was heated at reflux for 24 hours. The solution was cooled and the product was collected. Recrystallization from MeCN afforded 3.63 g (50%) of 2-acetylpyridine 4-(1-adamantyl)-3-thiosemicarbazone, mp 172°-173° C.

Analysis Calcd. for $C_{18}H_{24}N_4S$: C, 65.82; H, 7.36; N, 17.06; S, 9.76. Found: C, 66.04; H, 7.22; N, 16.88; S, 9.71.

Example 13

2-Acetylpyridine 4,4-dimethyl-3-thiosemicarbzone (Procedure A)

To a solution of 2.39 g (0.02 mol) of 4,4-dimethyl-3-thiosemicarbazide in 75 ml of EtOH was added 2.54 g (0.021 mol) of 2-acetylpyridine. After heating at reflux for eight hours, the solution was cooled and the product was collected. Recrystallization from MeOH afforded 1.2 g (26%) of 2-acetylpyridine 4,4-dimethyl-3-thiosemicarbazone, mp 149°–150° C.

Analysis Calcd. for $C_{15}H_{22}N_4S$: C, 62.03; H, 7.64; N, 19.29; S, 11.04. Found: C, 62.14; H, 7.64; N, 19.14; S, 11.16.

UTILITY

The compositions of this invention possess medicinal activity. More specifically, evidence indicates that all the compositions and their pharmaceutically-acceptable acid addition salts are active against viruses such as *herpes simplex* virus type 1; *herpes simplex* virus type 2; and *varicella-zoster* virus or other viruses amenable and responsive to topical treatment.

TABLE 1

TABLE AND DESCRIPTION OF THE FIGURES
ANTIVIRAL ACTIVITY OF 2-ACETYLPYRIDINE THIOSEMICARBAZONES

| DRUG Number | IN VITRO TESTS 50% Inhibitory Concentration (ug/ml) | | | | | | IN VITRO TESTS | | | | |
|---|---|---|---|---|---|---|---|---|---|---|---|
| | Viral Replication | | Cellular Protein and DNA Synthesis | | | | Apparent Therapeutic Indices | | Dermal Toxicity | Reduction of Lesions Guinea Pigs[3] | |
| | HSV-1 | HSV-2 | Incorp. of $^3$H amino Acids | Lowry Protein Assay | Incorp. of $^3$H thymidine | Diphenyl amine DNA Assay | HSV-1 | HSV-2 | Guinea Pigs[2] | Yes | No |
| 1 | 0.21 | 0.08 | 1.7 | 1.1 | 0.4 | 0.8 | 4.8 | 12.5 | +++ | Y | |
| 2 | 0.26 | | 2.0 | 1.3 | 1.4 | 2.1 | 6.5 | | 0 | | |
| 3 | 0.49 | 0.11 | 1.0 | 0.8 | 0.75 | 0.99 | 1.8 | 8 | +++ | Y | |
| 4 | 5.4 | | 28 | 22 | 7 | 8 | 3 | | + | | |
| 5 | 0.08 | 0.17 | 2.0 | 2.1 | 0.24 | 1.8 | 19 | 9 | +++ | Y | |
| 6 | 4.6 | 0.15 | 9.1 | 14 | 6.4 | 37 | 3.6 | 111 | ++ | | N |
| 7 | 0.22 | 0.05 | 0.25 | 0.29 | 0.32 | 0.33 | 1.4 | 6 | + | | N |
| 8 | 0.14 | 0.1 | 32 | 22 | 0.9 | 10 | 114 | 160 | 0 | Y | |
| 9 | 1.1 | 0.9 | 16 | 25 | 2.0 | 6.8 | 11 | 14 | + | Y | |

[1]The Apparent Therapeutic Index is calculated by dividing the average 50% inhibitory concentration for cellular protein and DNA synthesis by the 50% inhibitory concentration for viral replication.
[2]Scoring System for Dermal Toxicity: 0 = none, ± = very slight, + = slight, ++ = moderate, +++ = severe.
[3]A yes (Y) response indicates a statistically significant reduction in lesion score.

Analysis Calcd. for $C_{10}H_{14}N_4S$: C, 54.03; H, 6.35; N, 25.20; S, 14.42. Found: C, 53.83; H, 6.74; N, 25.25; S, 14.72.

Example 14

2-Acetylpyridine 4,4-dimethyl-3-thiosemicarbazone (Procedure B)

Methyl 3-[1-(2-pyridyl)ethylidene]hydrazinecarbodithioate (9.02 g, 0.04 mol) in 30 ml of EtOH was combined with 5.2 g (0.08 mol) of dimethylamine (40% aqueous solution). The resulting solution was heated at reflux for 24 hours and the excess dimethylamine was removed under water-pump aspiration for 15 minutes. The solution was filtered and cooled to give 7.3 g (82%) of bright yellow crystals of 2-acetylpyridine 4,4-dimethyl-3-thiosemicarbazone, mp 155°–156° C. whose infrared spectrum was identical to that of the product made by the method described in Example 13.

Example 15

1-Azacycloheptane-1-thiocarboxylic acid 2-[1-(2-pyridyl)propylidene]hydrazide (Procedure B)

Methyl 3-[1-(2-pyridyl)propylidene]hydrazinecarbodithioate (4.77 g, 0.02 mol) hexamethylenimine in 25 ml of MeOH were heated under reflux for 48 hours followed by overnight refrigeration. The solid material which separated from solution was collected by filtration and recrystallization from MeOH to afford 3.65 g (63%) of yellow crystalline 1-azacycloheptane-1-thiocarboxylic acid 2-[1-2-pyridyl)propylidene]hydrazide, mp 117°–119° C.

We claim:

1. A composition of matter useful for the topical treatment of a herpes virus in the tissue of an animal comprising a therapeutically-effective amount of:

(a) a 2-acetylpyridine thiosemicarbazone selected from the compounds represented by the formula

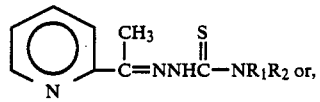

(b) a pharmaceutically-acceptable acid addition salt thereof wherein $R_1$ is hydrogen; alkyl having 1 to 12 carbon atoms; cycloalkyl having 3 to 10 carbon atoms; alkyl having 1 to 12 carbon atoms which is substituted by amino, alkylamino having 1 to 7 carbon atoms, dialkylamino having 1 to 7 carbon atoms in each alkyl group, cycloalkyl having 3 to 10 carbon atoms, hydroxy, C(O)Oalkyl having 1 to 7 carbon atoms in the alkyl group, phenyl, or pyridyl; alkenyl having 2 to 6 carbon atoms; alkynyl having 3 to 6 carbon atoms; benzyl which is substituted by methyl or phenyl on the alpha carbon atom, or substituted by methyl, dimethyl, halo, dihalo, or ethoxy on the phenyl ring; adamantyl; phenyl; naphthyl; phenyl or naphthyl which are mono-, di-, or trisubstituted by alkyl having 1 to 7 carbon atoms, halo, alkoxy having 1 to 7 carbon atoms, hydroxy, phenoxy, trifluoromethyl, dimethylamino, diethylaminomethyl, or C(O)Oalkyl having 1 to 7 carbon atoms in the alkyl group; pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino which is either bridged by an ethylene group, or is fused to a phenyl ring,, or is attached by a spiro linkage to an ethylene ketal group;
(2) homopiperazinyl; homopiperazinyl substituted with alkyl having 1 to 7 carbon atoms; piperazinyl; or piperazinyl substituted with alkyl having 1 to 7 carbon atoms, dialkyl having 1 to 7 carbon atoms in each alkyl group, phenyl, C(O)Oalkyl having 1 to 7 carbon atoms in the alkyl group, trifluoromethylphenyl, halophenyl, benzyl, or pyridyl;
(3) alkylenimino which may contain one double bond and may be mono- or disubstituted with alkyl, hydroxy, phenyl, or benzyl; and
(4) morpholino; or dialkylmorpholino having 1 to 7 carbon atoms in each alkyl group; and
(c) a pharmaceutically-acceptable diol penetration-enhancing vehicle.

2. The composition of claim 1 wherein the vehicle is a lower alkanediol in an amount of from 95 to 99.9% by weight.

3. The composition of claim 2 wherein the lower alkanediol is 1,3-butanediol.

4. The composition of claim 3 wherein the 1,3-butanediol is in the amount of 97 to 99.9% by weight.

5. The composition of claim 4 wherein the 1,3-butanediol is in the amount of 99.3% by weight.

6. The composition of claim 2 wherein $R_1$ is hydrogen, alkyl of 1 to 12 carbon atoms; cycloalkyl of 3 to 10 carbon atoms; alkyl of 1 to 12 carbon atoms which is substituted by amino, alkylamino of 1 to 4 carbon atoms, dialkylamino having 1 to 4 carbon atoms in each alkyl group; cycloalkyl of 3 to 10 carbon atoms, hydroxy, C(O)Oalkyl having 1 to 4 carbon atoms in each alkyl group, phenyl, or pyridyl; alkenyl having 2 to 6 carbon atoms; alkynyl having 3 to 6 carbon atoms; benzyl which is substituted by a methyl or phenyl on the alpha carbon atom, or substituted by a methyl, dimethyl, halo, dihalo, or ethoxy on the phenyl ring; adamantyl; phenyl; naphthyl; phenyl or naphthyl which are mono-, di-, or trisubstituted by alkyl having 1 to 4 carbon atoms, halo, alkoxy having 1 to 4 carbon atoms, hydroxy, phenoxy, trifluoromethyl, dimethylamino, diethylaminomethyl, or C(O)Oalkyl having 1 to 4 carbon atoms in the alkyl group; pyrdiyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of: azetidino; pyrrolidino; 2,5-dimethylpyrrolidino; piperidino;

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethyl piperidino; 3,5-dimethylpiperidino; morpholino; 3,5-dimethylmorpholino;

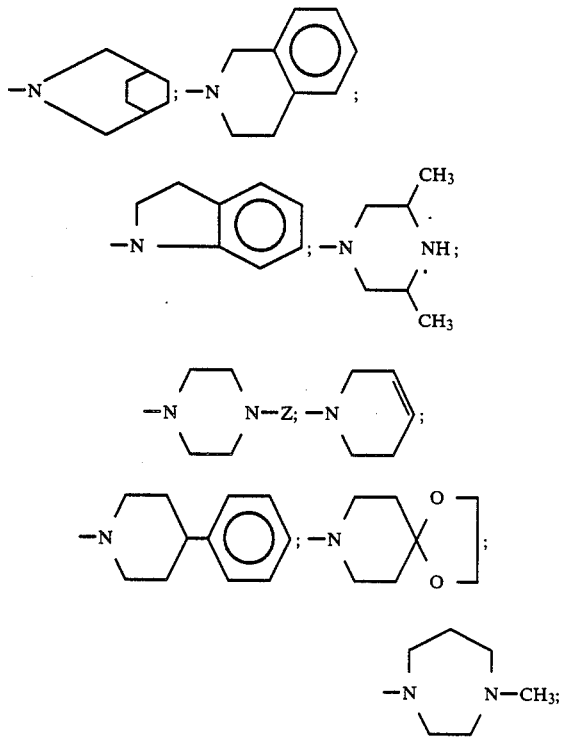

and azacyclotridecyl, wherein Z is methyl, phenyl, 3-trifluoromethylphenyl, benzyl, C(O)OEt, 3-pyridyl, 2-pyridyl, or 4-fluorophenyl.

7. The composition of claim 6 wherein the 2-acetylpyridine thiosemicarbazone is selected from the compounds selected from the group consisting of, 1-Azacycloheptane-1-thiocarboxylic acid 2-1-(2-pyridyl)ethylidene hydrazide; 2-Acetylpyridine 4-(3-fluorophenyl)-3-thiosemicarbazone; 3-Azabicyclo[3.2.2]nonane-3-thiocarboxylic acid 2-[1-(2-pyridyl)ethylidene]hydrazide; 1-Methylamino-1-deoxy-D-glucitol-N-thiocarboxylic acid 2-[1-(2-pyridyl)ethylidene]hydrazide; 2-Acetylpyridine 4,4-dimethylthiosemicarbazone; 2-Acetylpyridine 4-(1-adamantyl)thiosemicarbazone; 2-Acetylpyridine 4-cyclohexyl-4-methylthiosemicarbazone; 2-Acetylpyridine 4-methylthiosemicarbazone; 2-Acetylpyridine thiosemicarbazone; Azetidine-1-thiocarboxylic acid 2-[1-82-pyridyl)ethylidene]hydrazide; 1-Azacyclopentane-1-thiocarboxylic acid 2-[1-(2-pyridyl)ethylidene]hydrazide; Piperidine-1-thiocarboxylic acid 2-[1-(2-pyridyl)ethylidene]hydrazide; 2-Methylpiperidine-1-thiocarboxylic acid 2-[1-(2-pyridyl)ethylidene]hydrazide; 2-Ethylpiperidine-1-thiocarboxylic acid 2-[1-(2-pyridyl)ethylidene]hydrazide; 1-Azacyclotridecane-1-thiocarboxylic acid 2-[1-(2-pyridyl)ethylidene]hydrazide; 2-Acetylpyridine 4-allyl-3-thiosemicarbazone; 2-Acetylpyridine 4-(2-picoly)-3-thiosemicarbazone; 2-Acetylpyridine 4-cyclohexyl-3-thiosemicarbazone; 2-Acetylpyridine 4-phenyl-3-thiosemicarbazone; 2-Acetylpyridine 4-(1,1,3,3-tetramethylbutyl)-3-thiosemicarbazone; 1,4-Diaza-4-carboethoxycyclohexane-1-thiocarboxylic acid 2-[1-(2-pyridyl)ethylidene]hydrazide; 1,4-Diaza-4-phenycyclohexane-1-thiocarboxylic acid 2-[1-(2-pyridyl)ethylidene]hydrazide; 2-Acetylpyridine 4-(2-methylbenzyl)-3-thiosemicarbazone; 2-

Acetylpyridine 4-(4-trifluoromethyl-phenyl)-3-thiosemicarbazone; 1,4-Diaza-4-(2-pyridyl)cyclohexane-1-thiocarboxylic acid 2-[1-(2-pyridyl)ethylidene]hydrazide; 1,4-Diaza-4-(2-pyridyl(cyclohexane-1-thiocarboxylic acid 2-[1-(2-pyridyl)ethylidene hydrazide]dihydrochloride; 2-Acetylpyridine 4-benzyl-3-thiosemicarbazone; 1,4-Diaza-4-methylcycloheptane-1-thiocarboxylic acid 2-[1-(2-pyridyl)ethylidene]hydrazide; 2-Acetylpyridine 4-(2-propynyl)-3-thiosemicarbazone; 2-Acetylpyridine 4,4-dibutylthiosemicarbazone; 2-Acetylpyridine 4-ethylthiosemicarbazone; 2-Acetylpyridine 4-butylthiosemicarbazone; 2-Acetylpyridine 4-octylthiosemicarbazone; 2-Acetylpyridine 4-decylthiosemicarbazone; 2-Acetylpyridine 4-(2-phenethyl)thiosemicarbazone; (4-Hydroxy-4-phenylpiperidine-1-thiocarboxylic acid 2-[1-(2-pyridyl)ethylidene]hydrazide; 2-Acetylpyridine 4-(3-pinylmethyl)thiosemicarbazone; and 1-Azacyclononane-1-thiocarboxylic acid 2-[1-(2-pyridyl)ethylidene]hydrazide.

8. The composition of claim 7 wherein the 2-acetylpyridine thiosemicarbazone is selected from the group consisting of: 1-Hexahydroazepin-1-thiocarboxylic acid 2-[1-(2-pyridyl)ethylidene]hydrazide; 2-Acetylpyridine 4-(3-fluorophenyl)thiosemicarbazone; 3-Azabicyclo[3.2.2]nonane-3-thiocarboxylic acid 2-[1-(2-pyridyl)ethylidene]hydrazide; 1-Methylamino-1-deoxy-D-glucitol-N-thiocarboxylic acid 2-[1-(2-pyridyl)ethylidene]hydrazide; 2-Acetylpyridine 4,4-dimethylthiosemicarbazone; 2-Acetylpyridine 4-(1-adamantyl)thiosemicarbazone; 2-Acetylpyridine 4-cyclohexyl-4-methylthiosemicarbazone; 2-Acetylpyridine 4-methylthiosemicarbazone; and 2-Acetylpyridine thiosemicarbazone.

9. The composition of claim 8 wherein the thiosemicarbazone is 1H-hexahydroazepin-1-thiocarboxylic acid 2-[1-(2-pyridyl)ethylidene]hydrazide.

10. The composition of claim 8 wherein the 2-acetylpyridine thiosemicarbazone is 2-acetylpyridine 4-(3-fluorophenyl)thiosemicarbazone.

11. The composition of claim 8 wherein the thiosemicarbazone is 3-azabicyclo[3.2.2]nonane-3-thiocarboxylic acid 2-(1-(2-pyridyl)ethylidene]hydrazide.

12. The composition of claim 8 wherein the thiosemicarbazone is 1-methylamino-1-deoxy-D-glucitol-N-thiocarboxylic acid 2-[1-(2-pyridyl)ethylidene]hydrazide.

13. The composition of claim 8 wherein the 2-acetylpyridine thiosemicarbazone is 2-acetylpyridine 4,4-dimethylthiosemicarbazone.

14. The composition of claim 8 wherein the 2-acetylpyridine thiosemicarbazone is 2-acetylpyridine 4-(1-adamantyl)thiosemicarbazone.

15. The composition of claim 8 wherein the 2-acetylpyridine thiosemicarbazone is 2-acetylpyridine 4-cyclohexyl-4-methylthiosemicarbazone.

16. The composition of claim 8 wherein the 2-acetylpyridine thiosemicarbazone is 2-acetylpyridine 4-methylthiosemicarbazone.

17. The composition of claim 8 wherein the 2-acetylpyridine thiosemicarbazone is 2-acetylpyridine thiosemicarbazone.

18. The composition of claim 1 wherein $R_1$ is hydrogen and $R_2$ is —$CH_2CH$=$CH_2$.

19. The composition of claim 1 wherein $R_1$ is hydrogen and $R_2$ is

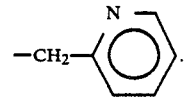

20. The composition of claim 1 wherein $R_1$ is hydrogen and $R_2$ is cyclohexyl.

21. The composition of claim 1 wherein $R_1$ is hydrogen and $R_2$ is isooctyl.

22. The composition of claim 1 wherein $R_1$ is hydrogen and $R_2$ is 3-fluorophenyl.

23. The composition of claim 1 wherein $R_1$ is hydrogen and $R_2$ is

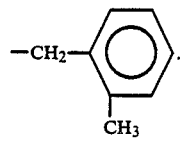

24. The composition of claim 1 wherein $R_1$ is hydrogen and $R_2$ is 4-trifluoromethylphenyl.

25. The composition of claim 1 wherein $R_1$ is hydrogen and $R_2$ is benzyl.

26. The composition of claim 1 wherein $R_1$ is hydrogen and $R_2$ is —$CH_2C$≡$CH$.

27. The composition of claim 1 wherein $R_1$ is ethyl and $R_2$ is ethyl.

28. The composition of claim 1 wherein $R_1$ is hydrogen and $R_2$ is ethyl.

29. The composition of claim 1 wherein $R_1$ is hydrogen and $R_2$ is butyl.

30. The composition of claim 1 wherein $R_1$ is hydrogen and $R_2$ is hexyl.

31. The composition of claim 1 wherein $R_1$ is hydrogen and $R_2$ is n-octyl.

32. The composition of claim 1 wherein $R_1$ is hydrogen and $R_2$ is decyl.

33. The composition of claim 1 wherein $R_1$ is hydrogen and $R_2$ is

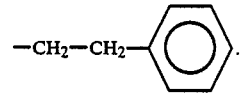

34. The composition of claim 1 wherein $R_1$ is hydrogen and $R_2$ is phenyl.

35. The composition of claim 1 wherein $NR_1R_2$ is

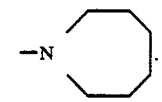

36. The composition of claim 1 wherein $NR_1R_2$ is

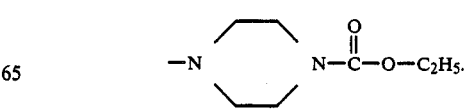

37. The composition of claim 1 wherein $NR_1R_2$ is

38. The composition of claim 1 wherein $NR_1R_2$ is

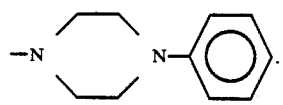

39. The composition of claim 1 wherein $NR_1R_2$ is

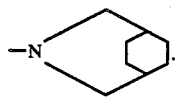

40. The composition of claim 1 wherein $NR_1R_2$ is

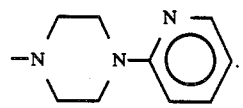

41. The composition of claim 1 wherein $NR_1R_2$ is

42. The composition of claim 1 wherein $NR_1R_2$ is

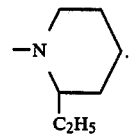

43. The composition of claim 1 wherein $NR_1R_2$ is

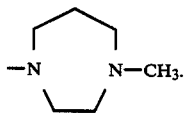

44. The composition of claim 1 wherein $NR_1R_2$ is

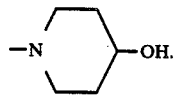

45. The composition of claim 1 wherein $NR_1R_2$ is

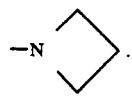

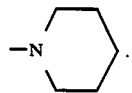

46. The composition of claim 1 wherein $NR_1R_2$ is

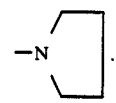

47. The composition of claim 1 wherein $NR_1R_2$ is

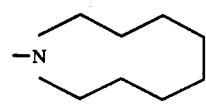

48. The composition of claim 1 wherein $NR_1R_2$ is

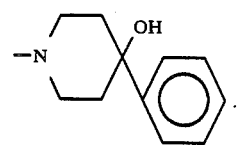

49. A pharmaceutical composition useful for the topical treatment of a herpes virus comprising a therapeutically-effective amount of:
(a) a 2-acetylpyridine thiosemicarbazone selected from the compounds represented by the formula

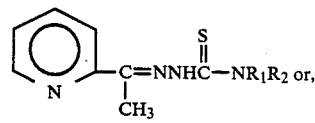

(b) a pharmaceutically-acceptable acid addition salt thereof wherein $R_1$ is hydrogen; alkyl having 1 to 12 carbon atoms; cycloalkyl having 3 to 10 carbon atoms; alkyl having 1 to 12 carbon atoms which is substituted by amino, alkylamino having 1 to 7 carbon atoms, dialkylamino having 1 to 7 carbon atoms in each alkyl group, cycloalkyl having 3 to 10 carbon atoms, hydroxy, C(O)Oalkyl having 1 to 7 carbon atoms in the alkyl group, phenyl, or pyridyl; alkenyl having 2 to 6 carbon atoms; benzyl which is substituted by methyl or phenyl on the alpha carbon atom, or substituted by alkyl having 1 to 7 carbon atoms, dialkyl having 1 to 7 carbon atoms in each alkyl group, halo, dihalo, or alkoxy on the phenyl ring; adamantyl; phenyl; naphthyl; phenyl or naphthyl which are mono-, di, or trisubstituted by alkyl having 1 to 7 carbon atoms, halo, alkoxy having 1 to 7 carbon atoms, hydroxy, phenoxy, trifluoromethyl, dialkylamino having 1 to 7 carbon atoms in each alkyl group, or C(O)Oalkyl having 1 to 7 carbon atoms in the alkyl group; and pyridyl; and $R_2$ is hydrogen or is selected from the group of radicals listed above for $R_1$, in which case $R_1$ and $R_2$ may be the same or different; and
(c) a pharmaceutically-acceptable diol penetration-enhancing vehicle.

50. The composition of claim 49 wherein the vehicle is a lower alkanediol in an amount of from 95 to 99.9% by weight.

51. The composition of claim 49 wherein the lower alkanediol is 1,3-butanediol.

52. The composition of claim 51 wherein 1,3-butanediol is in the amount of 97 to 99.9% by weight.

53. The composition of claim 52 wherein 1,3-butanediol is in the amount of 99.3% by weight, 54. The composition of claim 52 wherein NR₁R₂ is selected from the group consisting of —NH₂, —NHCH₃, —NH—CH₂CH=CH₂,

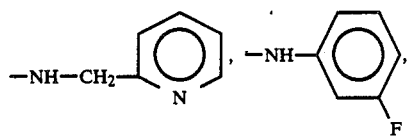

—N—CH₂—(CHOH)₄CH₂OH, —N(CH₃)₂, —NH—adamantyl,
|
CH₃

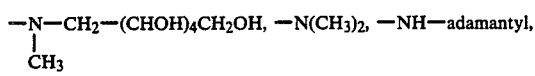

—NHC(CH₃)₂CH₂C(CH₃)₃, 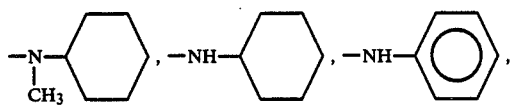

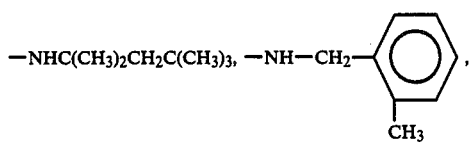

—NHCH₂C≡CH,  —N(C₂H₅)₂,  —NH(C₂H₅),
—NHC₄H₉, —NHC₈H₁₇, —NHC₁₀H₂₁,

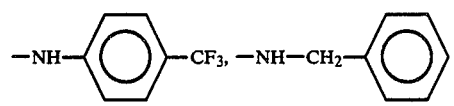

55. The composition of claim 53 wherein NR₁R₂ is selected from the group consisting of —NH₂, —NHCH₃, —NHCH₂CH=CH₂, and

56. The composition of claim 53 wherein NR₁R₂ is —NH₂.

57. The composition of claim 53 wherein NR₁R₂ is —NHCH₃.

58. The composition of claim 53 wherein —NR₁R₂ is —NHCH₂—CH=CH₂.

59. The composition of claim 53 wherein —NR₁R₂ is

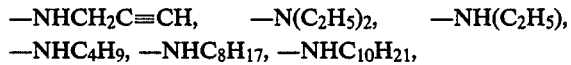

60. A method of topically treating a herpes virus infection in an animal comprising applying to the tissue of said animal a therapeutically-effective amount of a composition of claim 1.

61. A method in accordance with claim 60 wherein the topical treatment is effected prior to infection.

62. A method in accordance with claim 60 wherein the topical treatment is effected subsequent to infection.

63. The method of claim 60 wherein the virus is selected from the group consisting essentially of *herpes simplex* virus-1; *herpes simplex* virus-2; and *varicella-zoster* virus.

64. The method of claim 63 wherein the virus is *varicella-zoster* virus.

65. The method of claim 63 wherein the virus is selected from the group consisting of *herpes simplex* virus-1 and *herpes simplex* virus-2.

66. The method of claim 65 wherein the virus is *herpes simplex* virus-1.

67. The method of claim 65 wherein the virus is *herpes simplex* virus-2.

68. The method of claim 60 wherein said animal is a human patient.

* * * * *

UNITED STATES PATENT AND TRADEMARK OFFICE
CERTIFICATE OF CORRECTION

PATENT NO. : 4,777,166

DATED : October 11, 1988

INVENTOR(S) : Charles Shipman, Jr.; Daniel L. Klayman; Sandra H. Smith; John C. Drach; and Gordon L. Flynn It is certified that error appears in the above-identified patent and that said Letters Patent is hereby corrected as shown below:

Title page:

line 4, "[75] Inventors: Sandra H. Smith; John C. Drach; Gordon L. Flynn, all of Ann Arbor, Mich." should be --[75] Inventors: Charles Shipman, Jr., Dexter, Mich.; Daniel L. Klayman, Chevy, Chase, Md.; Sandra H. Smith; John C. Drach; Gordon L. Flynn, all of Ann Arbor, Mich.--.

Title page, item [19] "Smith et al." should read --Shipman, Jr., et al--.

Signed and Sealed this

Twenty-first Day of February, 1989

Attest:

DONALD J. QUIGG

*Attesting Officer*  *Commissioner of Patents and Trademarks*